United States Patent [19]

Stratton et al.

[11] Patent Number: 5,051,353
[45] Date of Patent: Sep. 24, 1991

[54] PRESERVATION AND RESTORATION OF HEMOGLOBIN IN BLOOD SUBSTITUTES

[75] Inventors: Lewis P. Stratton, Greenville, S.C.; Martha C. Farmer, Glencoe, Ill.; Alan S. Rudolph, Bowie, Md.

[73] Assignee: The United States of America as represented by the Secretary of the Navy, Washington, D.C.

[21] Appl. No.: 233,303

[22] Filed: Aug. 9, 1988

[51] Int. Cl.$^5$ ............................................. A01N 1/00
[52] U.S. Cl. ............................................. 435/2
[58] Field of Search ............................................. 435/2

[56] References Cited

U.S. PATENT DOCUMENTS 4,425,334  1/1984  Hunt .
4,675,310  6/1987  Chapman et al. .

Primary Examiner—Werren B. Lone
Assistant Examiner—Margaret Argo

[57] ABSTRACT

A hemoglobin-containing blood substitute preparation is protected from oxidation to methemoglobin. The protected preparation comprises between 10 mM and 60 mM of a compound selected from the group consisting of glutathione (GSH), nicotinamide adenine dinucleotide (NADH), nicotine adenine dinucleotide phosphate (NADPH) and mixtures of these in the aqueous phase of a hemoglobin-containing fluid. Oxidized hemoglobin in a preparation can be restored by adding between 10 mM and 60 mM of a compound selected from the group consisting of glutathione (GSH), nicotinamide adenine dinucleotide (NADH), nicotine adenine dinucleotide phosphate (NADPH) and mixtures of these to a hemoglobin-containing fluid in which the hemoglobin has converted in whole or part to methemoglobin, and storing the fluid at storage temperatures for blood products above the freezing point of the fluid for a time sufficient to convert methemoglobin to hemoglobin.

11 Claims, 5 Drawing Sheets

PRESERVATION AND RESTORATION OF HEMOGLOBIN IN BLOOD SUBSTITUTES

BACKGROUND OF THE INVENTION

1. Field of the Invention

This invention relates to the preservation and restoration of hemoglobin as an oxygen transport vehicle in blood substitutes. More particularly, this invention relates to compositions and methods of restoring hemoglobin which has been converted to methemoglobin.

2. Description of the Prior Art

In many instances, oxygen is a toxic or otherwise destructive agent. A wide variety of compounds have been studied and used to prevent oxidative damage in biological systems. Metal ions such as the ferric ion are often catalysts in the production of oxidizing species in solution. Desferal, which is a specific chelator of this form of iron, has been used successfully to block the oxidative catalyst action of the ferric ion. Other chelators such as EDTA and ascorbate have been used to remove metal ion catalysts. Ascorbate is a frequently used antioxidant although it is known to produce $H_2O_2$ by reacting with oxyhemoglobin. Prooxidant effects have been reported at 0.5 mM ascorbate and antioxidant effects at 5 mM concentrations.

The conversion of $H_2O_2$ to hydroxyl and superoxide radicals usually results in oxidative damage to proteins and other important molecules in cells and their metabolic removal is an important step in protection of cells. Radical scavengers such as the carbohydrates glucose and mannitol have been shown by others to be effective in the removal of deleterious radicals.

Much work has been done over many years to develop a human blood substitute that will carry oxygen. The three approaches which have emerged as leaders in this endeavor are; modified hemoglobin, synthetic organic materials such as fluorocarbons and artificial red blood cells (RBC). Of these approaches, artificial red blood cells most closely approximate the normal physiological system.

One form of artificial red blood cell is formed by encapsulating a hemoglobin solution as the aqueous phase in a lipid membrane as the oil phase. This lipid encapsulated hemoglobin system is known as LEH. Some methods of preparation and use for these functional surrogate red blood cells are described by T. M. S. Chang, "Semipermeable Microcapsules", *Science*, 146, 524, (1964); L. Djordjevich, and I. F. Miller, "Synthetic Erythrocytes from Lipid Encapsulated Hemoglobin", *J. Exp. Hemat.* 8, 584, (1980); and C. A. Hunt, R. L. Burnette, R. D. MacGregor, A. E. Strubbe, D. T. Lau, N. Taylor and H. Kawada, "Synthesis and Evaluation of a Prototypal Artificial Red Cell", *Science*, 230, 1165, (1985).

One of the major barriers to the successful use of artificial red blood cells and other hemoglobin (Hb) based blood substitutes is a means for preserving the preparations against the oxidation of Hb during preparation and storage. The oxidized form of Hb, methemoglobin (metHb), will not transport oxygen, and the accumulation of metHb often results in the precipitation of protein in the form of Heinz bodies, Bunn, *Semin. Hematol.*, 9:3, (1972). Oxidative damage is also the principle limiting factor in long-term storage of Hb based blood substitutes including LEH.

The above cited studies do not address the question of methemoglobin formation and make no attempt to prevent or reverse its formation from hemoglobin. J. Szebeni, J. H. Breuer, J. G. Szelenyl, G. Bathori, G. Lelkes and S. R. Hollan, in "Oxidation and Denaturation of Hemoglobin Encapsulated in Liposomes", *Biochim. Biophys. Acta,* 798, 60, 1984, recognize that oxidation of hemoglobin to nonfunctional methemoglobin is a problem that must be solved in order to produce a functional artificial RBC.

Previous work has indicated that much of the oxidative damage to hemoglobin is induced via $H_2O_2$ generation and superoxide radicals. Chiu et al., *Free Radicals in Biology,* Vol. 5, pp.115–160, ed. L. Parker, Academic Press, (1982). Thus, such agents as catalase, superoxide dismutase (SOD), ascorbate, nicotinamide adenine dinucleotide/nicotine adenine dinucleotide phosphate (NADH/NADPH), and 3-ribosyluric acid have shown moderate protection of hemoglobin from oxidative damage from nitrites and radical producing agents. It is known that the oxidation of hemoglobin to methemoglobin is reversible in vivo, but this reversal has not been effected in an artificial RBC.

J. Szebeni, C. C. Winterbourn and R. W. Carrell, in "Oxidative Interactions Between Haemoglobin and Membrane Lipid, A Liposome Model", *Biochem. J.*, 220, 685, 1984, teach that oxidation of the lipid in the membrane and oxidation of the encapsulated hemoglobin are interrelated. The writers suggest that certain ingredients such as catalase and 5 mM glutathione (GSH) may help prevent this oxidation when using fresh RBC lysate to make the liposomes. They reported no effect by GSH when using purified hemoglobin although they noted that catalase was beneficial. They did not report studies showing that any of these additives were able to reduce methemoglobin levels. All of their studies were carried out at 37° C., which is not a favorable storage condition.

R. C. Smith and V. Nunn, in "Prevention by 3-N-Ribosyluric Acid of the Oxidation of Bovine Hemoglobin by Sodium Nitrite", *Arch. Biochem. Biophys.*, 232, 348, 1984, teach that 3-N-ribosyluric acid, ascorbic acid and 0.1 mM GSH prevented oxidation of hemoglobin by nitrite at 37° C. This oxidation protection was probably caused by interfering with the action of $H_2O_2$. They did not report any studies at 4° C., but at 37° C. none of the antioxidants they studied reversed the oxidation of methemoglobin and, even in the presence of the antioxidants, all of the hemoglobin was converted to methemoglobin within 15 hours.

Sehgal et al., "Control of Methemoglobin Formation in Stroma-Free Hemoglobin Solutions", *J. Surgical Research,* 31, pp.13–17, (1981), disclose that NADH and NADPH will reduce methemoglobin formation in stroma-free hemoglobin preparations used in total exchange transfusion studies in baboons. All work was done in vivo and no evaluation of methemoglobin formation in preparations stored at 4° C. was performed. Additional antioxidant agents such as ascorbate and glucose were also added to these preparations.

L. Djordjevich, J. Mayoral, I. F. Miller and A. D. Ivankovich, "Cardiorespiratory Effects of Exchange Transfusions with Synthetic Erythrocytes in Rats", *Critical Care Medicine,* 15, 318, 1987, employed low levels of glucose, L-ascorbic acid and GSH (between 0.3 and 1 mM) as substrates for methemoglobin-reducing enzymes. They did not report any effect of this in vivo treatment.

In both U.S. Pat. Nos. 4,425,334 and 4,612,370, Hunt suggests including an antioxidant in LEH preparations. Specifically, Hunt describes LEH preparations in which an antioxidant in the form of alpha-tocopherol is included in the oil or lipid phase of the LEH. Hunt does not suggest the incorporation of an antioxidant into the aqueous or Hb phase of the LEH. The production and stability of an effective LEH system will require protection from oxidative damage for both the lipid portion and the aqueous compartment of LEH.

SUMMARY OF THE INVENTION

Accordingly, an object of this invention is to prevent the oxidation of hemoglobin to methemoglobin during development, production and storage of hemoglobin-containing fluids.

Another object of this invention is to promote the conversion of methemoglobin to hemoglobin following oxidative damage in hemoglobin-containing fluids and preparations.

An additional object of this invention is to increase the efficiency of the production of oxygen carrying fluids and preparations by reducing the loss of oxygen carrying capacity caused by the conversion of hemoglobin to methemoglobin.

Yet another object of this invention is to increase the efficacy of oxygen carrying blood substitutes by minimizing, preventing or reversing the conversion of hemoglobin to methemoglobin.

Yet an additional object of this invention is to increase the "shelf life" of hemoglobin-containing fluids and preparations.

A further object of this invention is a method of recovering for practical use hemoglobin containing-fluids and preparations in which the hemoglobin has oxidized to methemoglobin.

Yet a further object of this invention is to provide an effective antioxidant for the aqueous phase of an LEH system.

These and other objects of the invention are accomplished by including between 10 mM and 60 mM glutathione (GSH), reduced nicotinamide adenine dinucleotide (NADH), nicotine adenine dinucleotide phosphate (NADPH) or mixtures of these in a hemoglobin-containing fluid or preparation. Hemoglobin which has been converted to methemoglobin can be fully or substantially restored by this treatment and storing the fluid or preparation at storage temperatures for blood products above the freezing point of the fluid or preparation for a time sufficient to convert methemoglobin to hemoglobin.

BRIEF DESCRIPTION OF THE DRAWINGS

A more complete appreciation of the invention will be readily obtained by reference to the following Detailed Description of the Invention and the accompanying drawings in which like numerals in different figures represent the same structures or elements, wherein:

FIG. 3 is a graph depicting the effect of catalase and glutathione on rate of bovine methemoglobin formation.

FIG. 4 is a graph depicting the effect of catalase, GSH and NADH on rate of bovine methemoglobin formation.

DESCRIPTION OF THE PREFERRED EMBODIMENT

Figure 1:
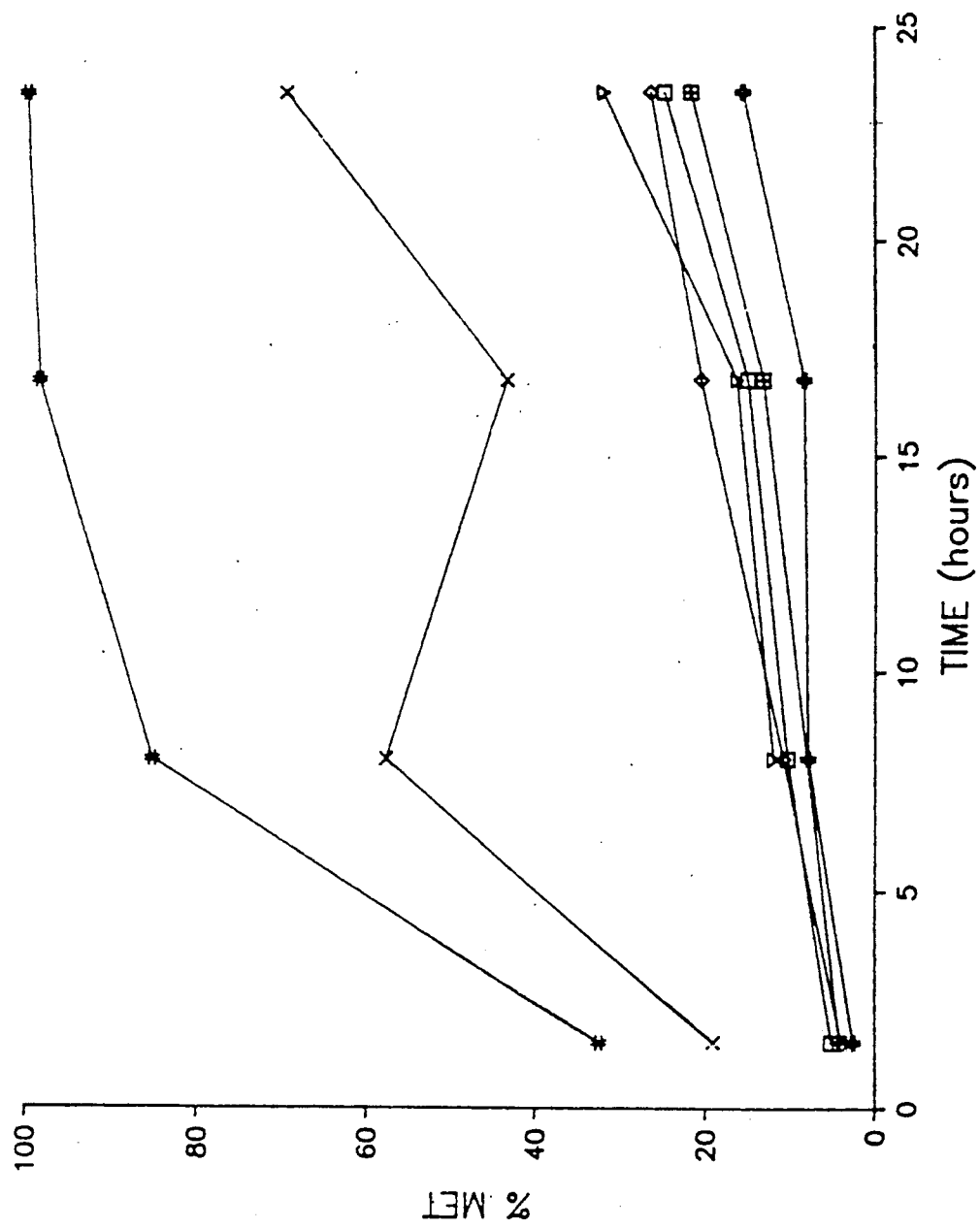
FIG. 1 is a graph depicting the effect of various antioxidants on the rate of human methemoglobin formation at 37° C.

The production and stability of a blood substitute system such as liposome encapsulated hemoglobin (LEH) will rely on the ability to protect both the encapsulated hemoglobin and the liposomal bilayer in the preparation from oxidative damage. We have found that the addition of between 10 mM and 60 mM preferably between 10 mM and 30 mM of any one of glutathione (GSH), nicotinamide adenine dinucleotide (NADH), nicotine adenine dinucleotide phosphate (NADPH) or mixtures of these to purified Hb-containing fluids or preparations results in the reduction in the rate of oxidative methemoglobin formation of hemoglobin at both in vivo temperatures of approximately 37° C. and storage temperatures for blood preparations. Hemoglobin containing-fluids include fluids containing unencapsulated Hb which are byproducts remaining after production of LEH. These fluids can be concentrated and reused.

When used as a mixed antioxidant, the ratio of active agents, such as GSH to NADH, is not critical but it is preferred that the ratio be 1:1. Other agents, such as catalase, superoxide dismutase (SOD), ascorbate, NADPH, and 3-ribosyluric acid may be present. These antioxidants remain with the aqueous phase of the LEH preparations.

More importantly, by the use of the formulations and methods of this invention, an actual reduction of the metHb content of an Hb preparation can be achieved thereby permitting the regeneration of previously unusable Hb preparations (with high methemoglobin levels). This regeneration can be accomplished by the addition of between 10 mM and 60 mM preferably between 10 mM and 30 mM glutathione (GSH), nicotinamide adenine dinucleotide (NADH), nicotine adenine dinucleotide phosphate (NADPH), or mixtures of these and the storage of the preparation at lower storage temperatures for a time sufficient to regenerate substantially all the hemoglobin.

The regeneration process works well at storage temperatures. With regard to this invention, storage temperatures are considered to be from just above the freezing point of the preparation to about room temperature of about 25° C. Preferred storage temperatures are from the freezing point to refrigeration temperatures of about 10° to 18° C. Most preferred are storage temperatures of about 4° C.

The regeneration process also takes time. The exact length of time is not critical but is likely to take more than 50 hours and may take 150 to 300 hours. The preparation can remain in storage for a year or more. By the compositions and methods of this invention the long-term storage of hemoglobin solutions and prevention of methemoglobin formation is achievable.

Now having generally described this invention, the following examples illustrate specific application of the invention. Tests were conducted using both human and bovine Hbs.

The human Hb was stroma-free hemolysate obtained from Letterman Army Institute of Research (San Francisco, Calif.) and the bovine Hb was from Biopure Corporation (Boston, Mass.). As stated by the manufacturer, the purity of the bovine preparation is >99% Hb in tris buffer with low pyrogenicity (0.01 EU/ml.). The bovine Hb does not contain detectable molecules greater than 68,000 daltons. Ascorbic acid and glutathione (GSH) were from Calbiochem (La Jolla, Calif.), Desferal (deferoxamine mesylate USP) was from CIBA-GEIGY (Summit, N.J.), n-octyl beta-D-glucopyranoside (OBG), ethylenediaminetetraacetic acid (EDTA), NADH and catalase were from Sigma Chemical Co. (St. Louis, Mo.), mannitol and trehalose were from Pfanstiel Laboratories (Waukegan, Ill.). All other chemicals were of reagent grade. Spectra were run on either a Beckman DU 8 or Cary 219 spectrophotometer.

Incubation of the hemoglobin preparations was carried out in sterilized 1.5 ml capped polyethylene Eppendorf microcentrifuge tubes containing equal volumes of test and Hb solutions, typically 150 ul of each, although this was increased for longer term experiments. Gas space in the tubes was air in all cases. Incubations were carried out at either 4° C. or 37° C. Aliquotes of 30 ul were taken for methemoglobin determination as described below. Unless otherwise noted 30 mM phosphate buffer, pH 7.4, was used for all solutions.

The assay used to determine the percent metHb was adapted from the method of Tomita, S., Y. Enoki, M. Santa, H. Yoshida and Y. Yasumitsu, *J. Nara. Med. Assoc.*, 19,1 (1968). Phosphate buffer, 1.96 ml, was added to 10 ul of 0.3M NaCN in a 1 cm cuvette, followed by 30 ul of the incubation mixture containing Hb. The cuvette was mixed by inversion, allowed to stand 10 minutes and scanned from 700 to 535 nM. Three or four crystals of $K_3Fe(CN)_6$ were dissolved in the cuvette which was again allowed to equilibrate for 5-10 minutes before scanning the same range. Alternatively, 20 to 40 ul of a 30 mM solution of $K_3Fe(CN)_6$ can be used in place of the crystals. The percent metHb was calculated using the equation and constants determined by Tomita cited above:

Percent Methemoglobin $= [1.778 - (0.778 \times E_1/E_2)] \times 100$ where:

$E_1$ = absorbance at 576 nM after addition of NaCN
$E_2$ = absorbance at 576 nM after addition of $K_3Fe(CN)_6$

EXAMPLE I

Hemoglobin was incubated for 24 hours at 37° C. in the presence of 5 mM concentrations of various antioxidants (FIG. 1) and the percentage of methemoglobin determined periodically using the method of Tomita, S., Y. Enoki, M. Santa, H. Yoshida and Y. Yasumitsu, *J. Nara. Med. Assoc.*, 19,1 1968. FIG. 1 illustrates the effect of (x) ascorbate, (#) desferal, ( ) EDTA, (+) glutathione, (▽) trehalose, (□) control, and ( ) mannitol on the rate of human methemoglobin formation at 37° C. incubation of human Hb. All antioxidants were present at 5 mM in pH 7.4, 30 mM phosphate buffer. GSH at 5 mM concentration caused a modest reduction in the rate of conversion to methemoglobin compared to the rate of conversion when incubated with buffer alone (16% compared to 25% after 24 hr.). Both desferal, an $Fe^{+3}$ chelator, and ascorbate greatly increased the methemoglobin formation rate when present at 5 mM. EDTA, mannitol and trehalose when tested at this concentration had no measurable effect.

At 37° C., higher concentrations of GSH (10 mM) resulted in a lower rate of metHb formation for both human and bovine Hb solutions. However, this concentration of GSH did not have a protective effect when added to dilute (1 mM) bovine Hb solutions. In these dilute solutions GSH caused effects like those of ascorbate and desferol (data not shown).

Other studies were carried out in buffers of different pH values (graph not shown). The rate of metHb formation in 10 mM GSH and in the controls was unaffected by the changes in pH in the range from 7.4 to 8.0.

EXAMPLE II

Figure 2:
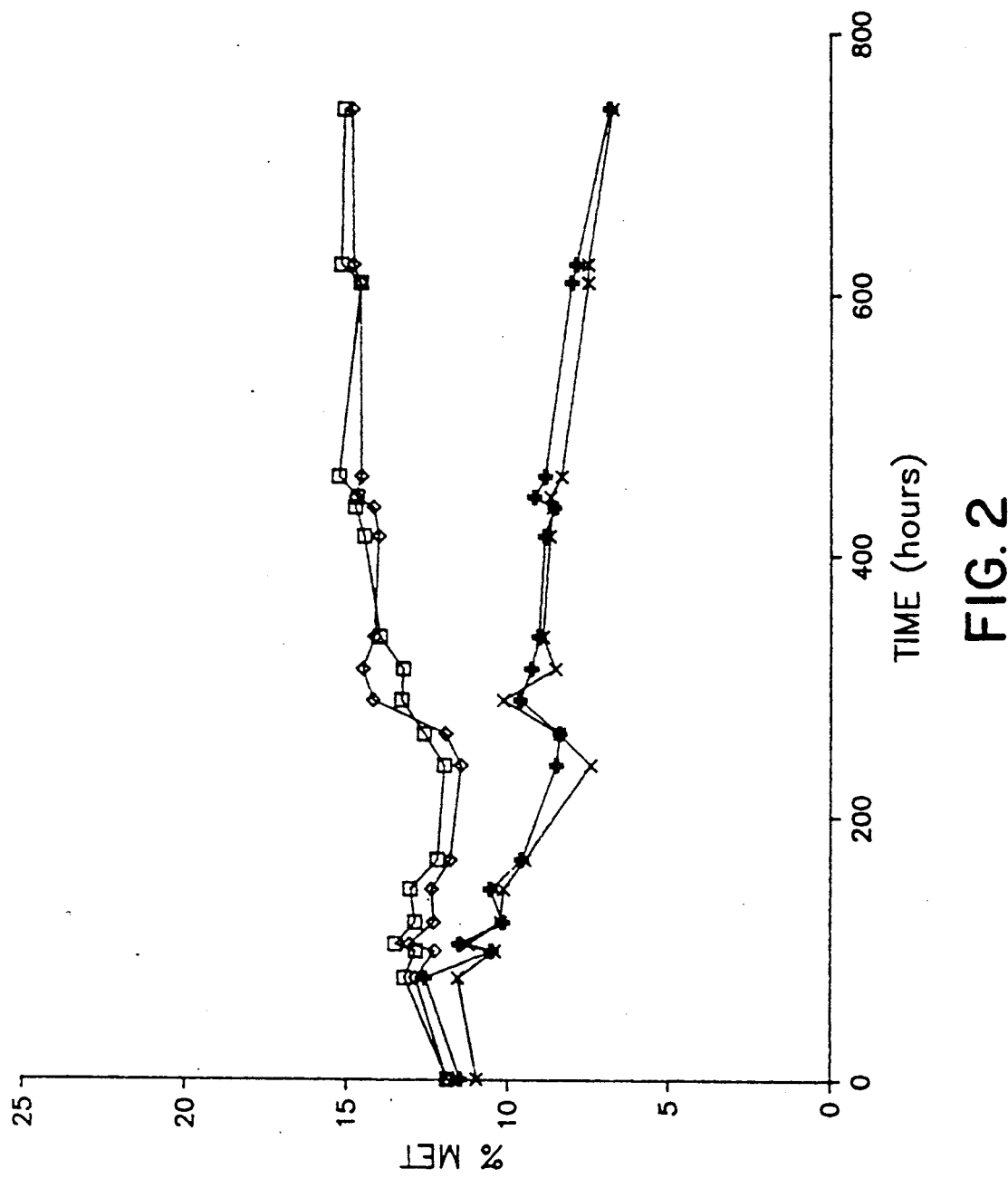
FIG. 2 is a graph depicting the effect of glutathione and glucose on rate of bovine methemoglobin formation at 4° C.

At 4° C. the presence of 10 mM glutathione caused a marked reduction in the amount of bovine metHb over a period of a month or more. FIG. 2 illustrates the effect of glutathione and glucose on reducing the concentration of bovine methemoglobin at 4° C. ((□) control, ( ) 10 mM glucose, (x) 10 mM GSH, (+) 10 mM glucose and 10 mM GSH). Significantly, addition of GSH to these samples resulted in an actual reduction in the amount of metHb (from 15% to 4%) within a few days, a trend that continued for the duration of the experiment (over 30 days). At 4° C., the GSH induced decrease in metHb was quite significant but not effected by the addition of glucose.

Figure 3A:
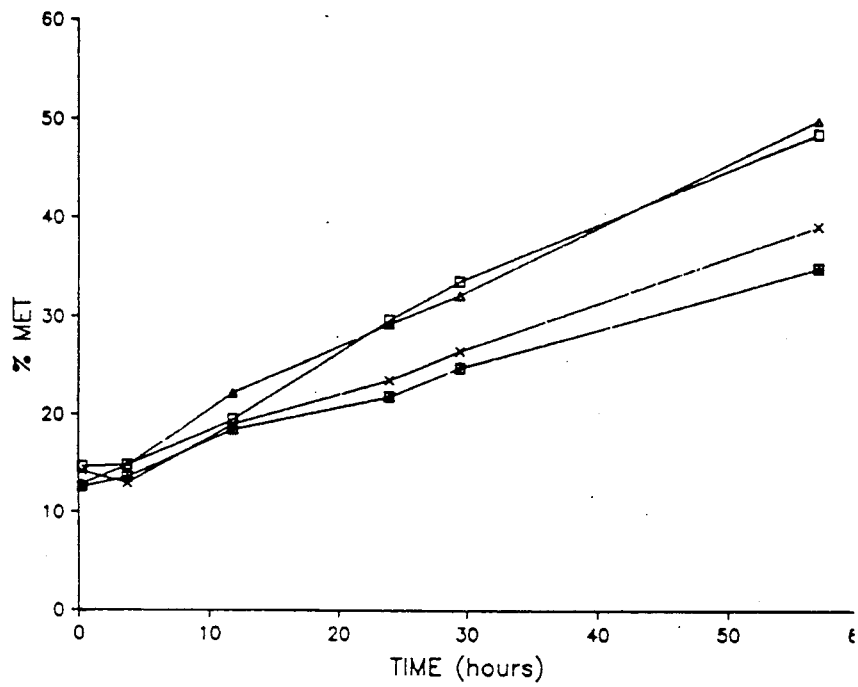
FIG. 3A at 37° C.
Figure 3B:
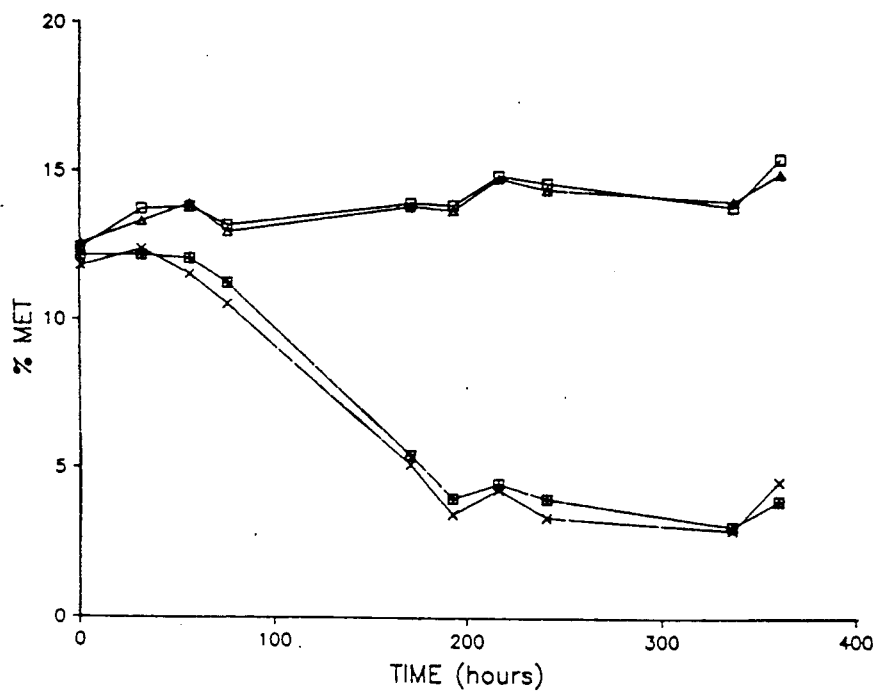
FIG. 3B at 4° C.

In another, study GSH at 10 mM concentration caused a marked reduction in the level of methemoglobin in a sample of purified bovine hemoglobin stored at 4° C. for 2 weeks as shown in FIG. 3B. Initially, the sample was 12% methemoglobin and after 360 hours the methemoglobin values were: (□) control, 15%; (x) 10 mM GSH, 5%; (Δ) 2600 U/ml catalase, 15%; ( ) GSH and catalase, 4%. Thus, catalase at 2600 U/ml had no effect at this temperature. In a similar demonstration of the method (no graph shown), a sample that started at 13% methemoglobin was reduced to 7% after 294 hours of incubation at 4° C. with either 10 mM GSH alone or with 10 mM GSH and 10 mM glucose.

EXAMPLE III

Purified bovine hemoglobin was incubated with 10 mM GSH at 37° C. with or without the addition of 10 mM glucose. The sample was 12% methemoglobin when the incubation started and after 33 hours the values were: GSH alone, 24%; GSH and glucose, 25%; glucose alone, 40%; and the control, 41% (graph not shown). In another demonstration shown in FIG. 3A, the enzyme catalase was used alone at 2600 U/ml and with 10 mM GSH. At the beginning, methemoglobin levels in the purified bovine hemoglobin were 14%, while after 57 hr. they were: GSH alone, 39%; catalase and GSH, 35%; catalase alone, 50%; and control, 48%. Thus, catalase at 2600 U/ml was ineffective alone and had only a very minor effect, if any, in the presence of GSH.

EXAMPLE IV

Figure 4A:
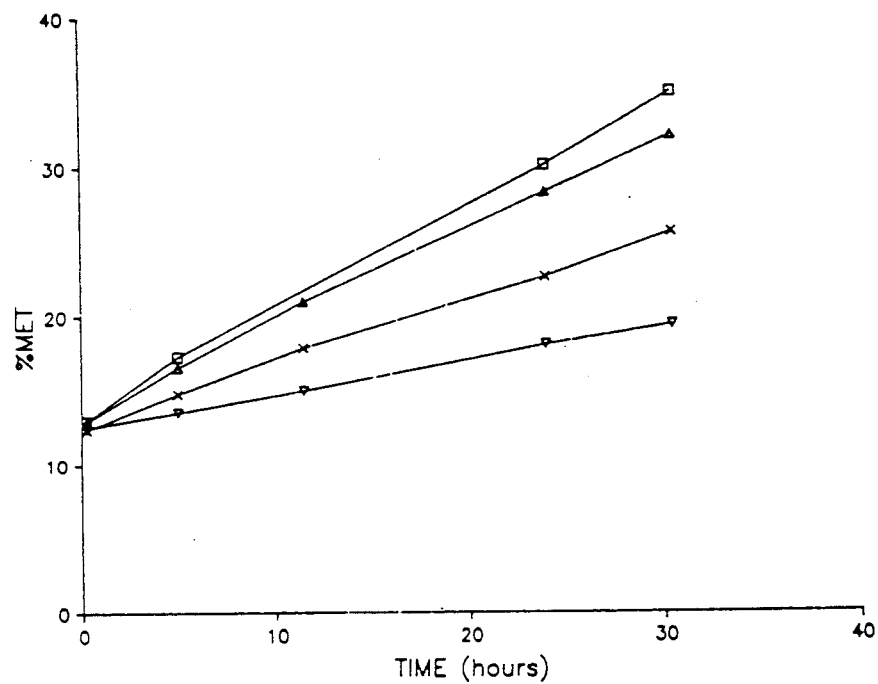
FIG. 4A at 37° C.

The most effective antioxidant tested for its ability to inhibit the rate of metHb formation was NADH. The addition of 10 mM NADH caused nearly a 50% reduction (19% metHb for NADH treated vs. 35% for the control after 30 hr.) in the rate of metHb formation when incubated with bovine Hb at 37° C. as shown in FIG. 4A [(□) control, (Δ) catalase, (x) GSH, (▽) NADH].

Figure 4B:
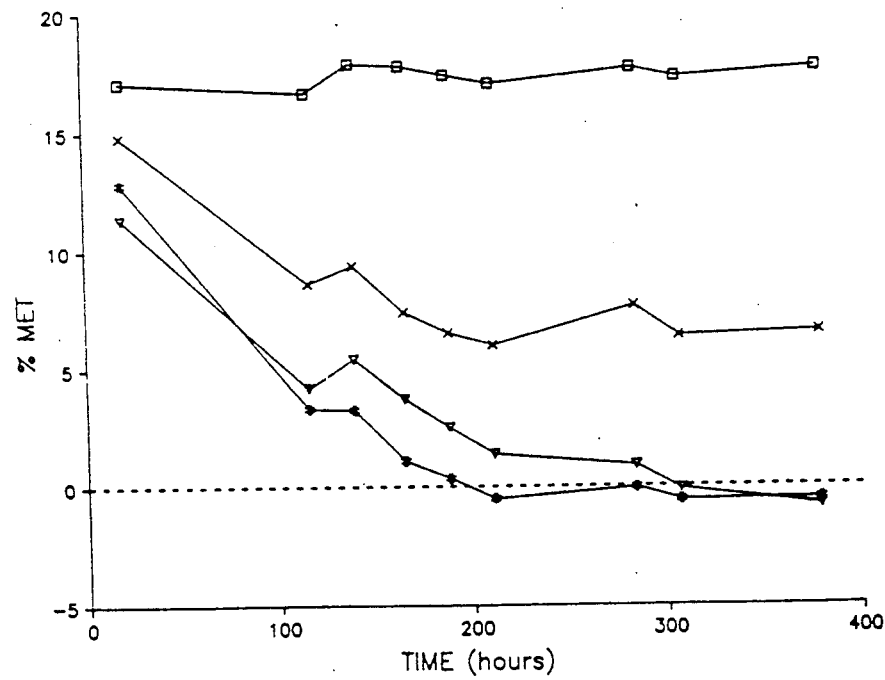
FIG. 4B at 4° C.

An additional example which shows the reduction in absolute amounts of methemoglobin in contrast to the reduction in rate of methemoglobin formation occurred when 10 mM NADH was tested. Purified bovine hemoglobin from which all protein greater than 68 Kd had been removed was stored at 4° C. with or without 10 mM NADH. Starting with about 13% methemoglobin the 10 mM NADH caused a decrease to undetectable levels over a 300 hour period as shown in FIG. 4B [(58) control, (▽) NADH, (x) GSH, (#) GSH & NADH] while the control rose slowly to about 17% and stayed at that level for 300 hours. GSH and NADH together caused a reduction to undetectable levels in 200 hours, an effect that was maintained for at least another 200 hrs. GSH alone caused a drop to 7% in 200 hrs and maintained that level for an additional 200 hours when the demonstration was terminated.

EXAMPLE V

Figure 5:
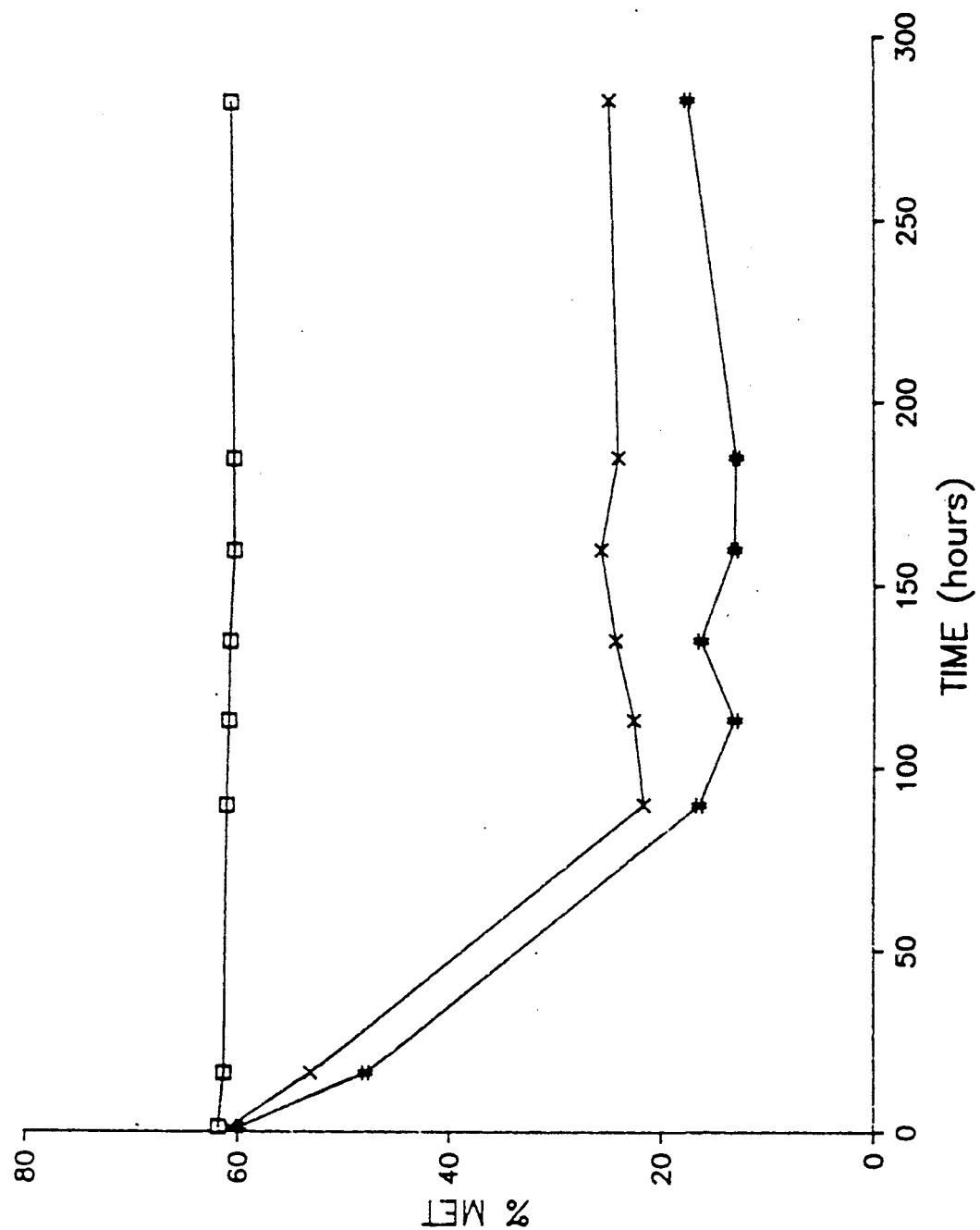
FIG. 5 is a graph depicting the effect of GSH and NADH on rate of human methemoglobin reduction at 4° C.

The most striking result observed was the reduction of metHb in a sample of human hemoglobin (not heat treated) that had been stored for a year at 4° C. as shown in FIG. 5 [(□) control, (x) GSH, (#) GSH & NADH]. The addition of GSH drastically reduced the amount of metHb in this sample from 60% to 10-15% in 80 hours. The combination of GSH and NADH resulted in even further reduction of methemoglobin in this stored sample. The addition of these two agents maintained this sample at these low metHb levels for the 12.5 day test period.

EXAMPLE VI

An example which illustrates the effect of GSH in the LEH occurred when a concentrated GSH solution was mixed with hemoglobin to give a final concentration of 15 mM and then the mixture was used to make LEH. After 32 hours at 37° C. (which accelerates the rate of conversion to methemoglobin), the hemoglobin from the control LEH's which had no GSH was 71% methemoglobin while the LEH's with 15 mM GSH contained 60% methemoglobin. In a related example, after 37 days at 4° C. LEH's prepared with hemoglobin solution which had a 30 mM GSH concentration contained 33% methemoglobin while the control LEH had 42% methemoglobin. In still another example LEH with 15 mM GSH had 21% metHb after 30 days while LEH with 60 mM GSH was 29% metHb and the control LEH with no GSH was 42%.

The methods and formulations of this invention provide a preserved hemoglobin based blood substitute, a method of reducing the rate of oxidation of hemoglobin, and a method of restoring hemoglobin-containing preparations where the hemoglobin was converted to methemoglobin.

Obviously, many modifications and variations of the present invention are possible in light of the above teachings. It is therefore to be understood that within the scope of the appended claims, the invention may be practiced otherwise than as specifically described.

What I claim is:

1. A hemoglobin blood substitute preparation including a compound in the aqueous phase of a hemoglobin-containing fluid, said compound selected from the group consisting of glutathione, and nicotinamide adenine dinucleotide (NADH) and mixtures of these and said glutathione being present in said aqueous phase in a concentration of 10 mM to 60 mM.

2. A blood substitute according to claim 1 wherein the compound consists of glutathione.

3. A blood substitute according to claim 1 wherein the concentration of said compound in said aqueous phase is between 10 mM and 60 mM.

4. A blood substitute according to claim 1 wherein the compound is a mixture of glutathione and nicotinamide adenine dinucleotide.

5. A blood substitute according to claim 1 wherein the concentration of the compound is between 10 mM and 20 mM.

6. A blood substitute according to claim 2 wherein the concentration of the compound is between 10 mM and 20 mM.

7. A blood substitute according to claim 3 wherein the concentration of the compound is between 10 mM and 20 mM.

8. A blood substitute according to claim 4 wherein the concentration of the compound is between 10 mM and 20 mM.

9. A hemoglobin blood substitute preparation including a compound in the aqueous phase of a hemoglobin-containing fluid, said compound comprising glutathione, and said glutathione being present in said aqueous phase in a concentration effective, at a temperature of from above the freezing point of said fluid to about 25° C., to reduce a significant amount of any methemoglobin in said fluid to hemoglobin upon storage of said solution at said temperature for about 300 hrs or less.

10. The blood substitute of claim 1, wherein said hemoglobin-containing fluid is a purified hemoglobin-containing fluid.

11. The blood substitute of claim 9, wherein said hemoglobin-containing fluid is a purified hemoglobin-containing fluid.

* * * * *